(12) United States Patent
Kase et al.

(10) Patent No.: US 8,212,862 B2
(45) Date of Patent: Jul. 3, 2012

(54) ENDOSCOPE SYSTEM

(75) Inventors: Seigo Kase, Hino (JP); Yasuhito Kura, Hachioji (JP); Yuji Sakamoto, Kunitachi (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/012,051

(22) Filed: Jan. 24, 2011

(65) Prior Publication Data

US 2011/0273549 A1 Nov. 10, 2011

Related U.S. Application Data

(63) Continuation of application No. PCT/JP2010/067949, filed on Oct. 13, 2010.

(30) Foreign Application Priority Data

Nov. 6, 2009 (JP) .................................. 2009-255185

(51) Int. Cl.
*A62B 1/04* (2006.01)
(52) U.S. Cl. .......................................... 348/68
(58) Field of Classification Search .............. 348/68–70; A62B 1/04
See application file for complete search history.

(56) References Cited

U.S. PATENT DOCUMENTS

| | | | | | |
|---|---|---|---|---|---|
| 4,678,900 | A | * | 7/1987 | Nishioka | 250/205 |
| 5,976,071 | A | * | 11/1999 | Sekiya | 600/111 |
| 6,425,858 | B1 | * | 7/2002 | Minami | 600/168 |
| 7,522,209 | B2 | * | 4/2009 | Wakashiro | 348/345 |
| 7,811,229 | B2 | * | 10/2010 | Sugimoto | 600/160 |
| 2003/0187319 | A1 | * | 10/2003 | Kaneko et al. | 600/9 |
| 2004/0220478 | A1 | | 11/2004 | Wallace et al. | |
| 2005/0010082 | A1 | | 1/2005 | Nishimura et al. | |

(Continued)

FOREIGN PATENT DOCUMENTS

EP 1 437 083 A1 7/2004

(Continued)

OTHER PUBLICATIONS

European Search Report dated Feb. 27, 2012 from corresponding European Patent Application No. EP 10 82 8173.4.

*Primary Examiner* — Tung Vo
(74) *Attorney, Agent, or Firm* — Scully, Scott, Murphy & Presser, P.C.

(57) ABSTRACT

An endoscope system of the present invention has an endoscope which acquires a direct-view field of view image and a side-view field of view image of an object to be observed, a light source apparatus which supplies an illuminating light for illuminating the object to be observed, a detection section which detects a change of a physical quantity with respect to movement of an insertion section provided at the endoscope, which occurs due to an operation of the endoscope, an image processing unit which generates and outputs a video signal including the direct-view field of view image and the side-view field of view image in a same screen, and a light adjustment area selection section which detects a brightness of the direct-view field of view image and a brightness of the side-view field of view image individually, selects a field of view image corresponding to a moving direction in which the change of the physical quantity increases out of the direct-view field of view image and the side-view field of view image as a light adjustment target based on a detection result of the detection section, and performs control so as to make a luminance of the field of view image selected as the light adjustment target relatively higher than a luminance of the other field of view image.

6 Claims, 9 Drawing Sheets

U.S. PATENT DOCUMENTS

| | | | |
|---|---|---|---|
| 2007/0134615 A1* | 6/2007 | Lovely | 433/29 |
| 2008/0009714 A1 | 1/2008 | Oda | |
| 2008/0045797 A1 | 2/2008 | Yasushi et al. | |
| 2008/0091065 A1* | 4/2008 | Oshima et al. | 600/109 |
| 2009/0041320 A1 | 2/2009 | Tanaka | |
| 2009/0198104 A1 | 8/2009 | Sugiyama | |

FOREIGN PATENT DOCUMENTS

| | | |
|---|---|---|
| EP | 1 769 718 A1 | 4/2007 |
| EP | 1 867 271 | 12/2007 |
| EP | 2 008 571 A1 | 12/2008 |
| EP | 2 082 678 A1 | 7/2009 |
| EP | 2 085 017 A1 | 8/2009 |
| JP | 60-053923 | 3/1985 |
| JP | 05-040231 | 2/1993 |
| JP | 06-181885 | 7/1994 |
| JP | 09-313435 | 12/1997 |
| JP | 10-165357 | 6/1998 |
| JP | 11-032982 | 2/1999 |
| JP | 2000-356749 | 12/2000 |
| JP | 2003-093328 | 4/2003 |
| JP | 2004-329700 | 11/2004 |
| JP | 2005-137701 A | 6/2005 |
| JP | 2006-235346 | 9/2006 |
| JP | 2007-282857 | 11/2007 |
| JP | 2007-307090 | 11/2007 |
| JP | 2007-330348 | 12/2007 |
| JP | 2008-136628 | 6/2008 |
| JP | 2008-309860 | 12/2008 |
| JP | 2009-045358 | 3/2009 |
| JP | 2009-178416 | 8/2009 |
| WO | WO 2006/004083 A1 | 1/2006 |
| WO | WO 2009/128055 A1 | 10/2009 |

* cited by examiner

DIRECT-VIEW FIELD OF VIEW IMAGE
(LIGHT ADJUSTMENT TARGET AREA)

SIDE-VIEW FIELD OF VIEW IMAGE
(NON-LIGHT ADJUSTMENT TARGET AREA)

SIDE-VIEW FIELD OF VIEW IMAGE
(LIGHT ADJUSTMENT TARGET AREA)

DIRECT-VIEW FIELD OF VIEW IMAGE
(NON-LIGHT ADJUSTMENT TARGET AREA)

DARK PART

ENDOSCOPE SYSTEM

CROSS REFERENCE TO RELATED APPLICATION

This application is a continuation application of PCT/JP2010/067949 filed on Oct. 13, 2010 and claims benefit of Japanese Application No. 2009-255185 filed in Japan on Nov. 6, 2009, the entire contents of which are incorporated herein by this reference.

BACKGROUND OF THE INVENTION

1. Field of the Invention

The present invention relates to an endoscope system, and particularly relates to an endoscope system capable of observing a direct-view direction and a side-view direction at the same time.

2. Description of the Related Art

Endoscope systems each including an endoscope which picks up an image of an object inside a subject, an image processing apparatus which generates an observed image of the object whose image is picked up by the endoscope, and the like are widely used in the medical field, the industrial field and the like.

For example, Japanese Patent Application Laid-Open Publication No. 2008-309860 discloses an optical system capable of simultaneously acquiring an object image in the direct-view direction corresponding to a center axis direction, and an omnidirectional object image in the side-view direction which is substantially orthogonal to the center axis direction, and an endoscope including the optical system. According to the endoscope including the optical system disclosed in Japanese Patent Application Laid-Open Publication No. 2008-309860, the image in the direct-view direction forming a circular shape (direct-view field of view image) and an image of an entire circumference in the side-view direction forming a ring shape (side-view field of view image) in the outer circumference of the image in the direct-view direction are displayed on a display section such as a monitor.

SUMMARY OF THE INVENTION

An endoscope system of the present invention has an endoscope which acquires a direct-view field of view image and a side-view field of view image of an object to be observed, a light source apparatus which supplies an illuminating light for illuminating the object to be observed, a detection section which detects a change of a physical quantity with respect to movement of an insertion section provided at the endoscope, which occurs due to operation of the endoscope, an image processing unit which generates an observed image including the direct-view field of view image and the side-view field of view image in a same screen, and outputs the observed image as a video signal, and a light adjustment area selection section which detects a brightness of the direct-view field of view image and a brightness of the side-view field of view image individually based on the video signal, selects a field of view image corresponding to a moving direction in which the change of the physical quantity increases out of the direct-view field of view image and the side-view field of view image as a light adjustment target based on a detection result of the detection section, and performs control so as to make a luminance of the field of view image selected as the light adjustment target relatively higher than a luminance of the other field of view image.

An endoscope system of the present invention has an endoscope which acquires a direct-view field of view image and a side-view field of view image of an object to be observed, a light source apparatus which supplies an illuminating light for illuminating the object to be observed, a detection section which detects projection of a treatment instrument from a treatment instrument channel provided in the endoscope, an image processing unit which generates an observed image including the direct-view field of view image and the side-view field of view image in a same screen, and outputs the observed image as a video signal, and a light adjustment area selection section which detects a brightness of the direct-view field of view image and a brightness of the side-view field of view image individually based on the video signal, selects a field of view image in a projection direction of the treatment instrument as a light adjustment target out of the direct-view field of view image and the side-view field of view image based on a detection result of the detection section, and performs control with respect to the light source apparatus so that a luminance of the field of view image selected as the light adjustment target becomes relatively higher than a luminance of the other field of view image.

DETAILED DESCRIPTION OF THE PREFERRED EMBODIMENTS

Hereinafter, embodiments of the present invention will be described with reference to the drawings.

First Embodiment

Figure 1:
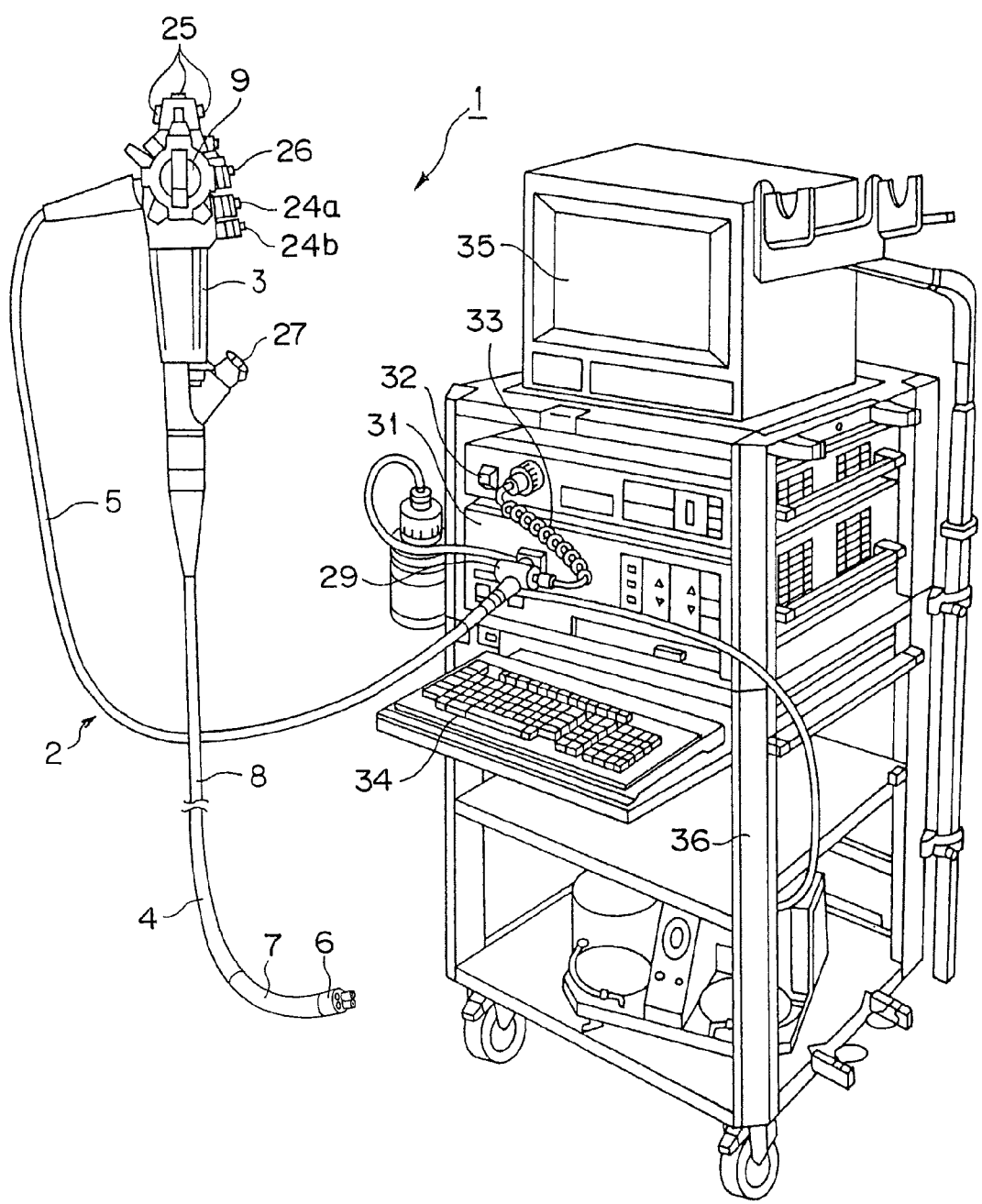
FIG. 1 is a view showing a configuration of an endoscope system according to an embodiment of the present invention.

As shown in FIG. 1, an endoscope system 1 has an endoscope 2 which picks up an image of an object to be observed and outputs an image pickup signal, a light source apparatus 31 which supplies an illuminating light for illuminating the object to be observed, a video processor 32 which generates and outputs a video signal corresponding to the image pickup signal, and a monitor 35 which displays an observed image corresponding to the video signal.

The endoscope 2 is configured by having an operation section 3 which is grasped by a surgeon to perform an operation, an elongated insertion section 4 which is formed at a distal end side of the operation section 3 and is inserted into a body cavity or the like, and a universal cord 5 with one end portion provided to be extended from a side portion of the operation section 3.

The insertion section 4 is configured by having a rigid distal end portion 6 provided at the most distal end side, a bending portion 7 which is bendable and provided at a rear end of the distal end portion 6, and a flexible tube portion 8 which is long, has flexibility and is provided at a rear end of the bending portion 7. Further, the bending portion 7 performs a bending motion corresponding to an operation of a bending operation lever 9 provided at the operation section 3.

Figure 2:
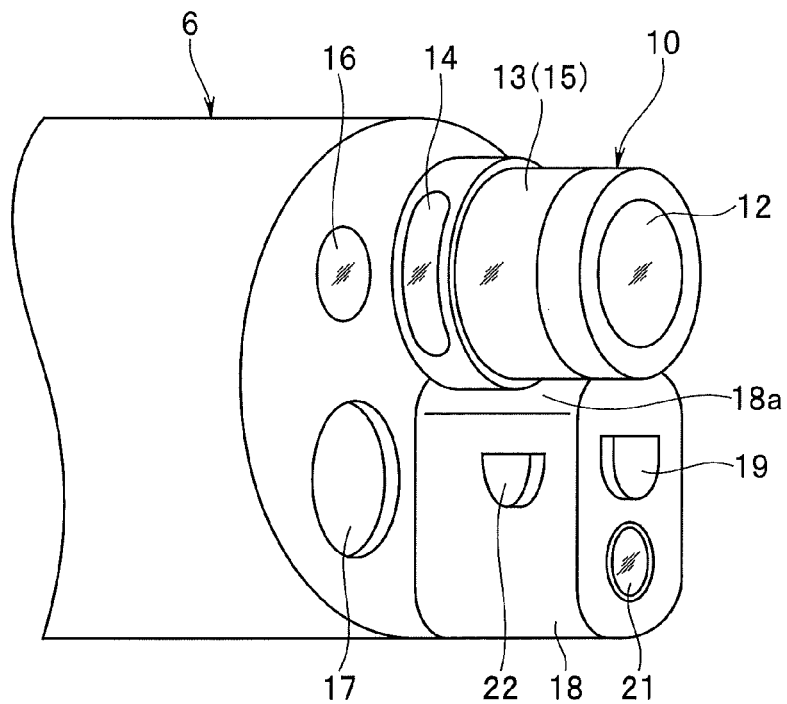
FIG. 2 is a perspective view showing a configuration of a distal end portion of an insertion section of the endoscope.

Meanwhile, as shown in FIG. 2, on the distal end portion 6 of the insertion section 4, a cylindrical portion 10 in a columnar shape is formed, which is provided to be projected from a position eccentric to an upper side from a center of a front end face of the distal end portion 6.

An objective optical system not illustrated which is used for both a direct-view and a side-view is provided at a distal end portion of the cylindrical portion 10. Further, the distal end portion of the cylindrical portion 10 is configured by having a direct-view observation window 12 which is disposed at a location corresponding to the direct-view direction of the aforesaid objective optical system not illustrated, and a side-view observation window 13 which is disposed at a location corresponding to the side-view direction of the aforesaid objective optical system not illustrated. Furthermore, a side-view illumination portion 14 which emits a light for illuminating the side-view direction is formed in the vicinity of a proximal end of the cylindrical portion 10.

The side-view observation window 13 includes a side-view mirror lens 15 for making a side-view field of view image acquirable by capturing a return light (reflected light) from an object to be observed which is incident from the circumferential direction in the cylindrical portion 10 in a columnar shape.

At an image formation position of the aforesaid objective optical system not illustrate, (an image pickup surface of) an image pickup device is assumed to be disposed so that an image of an object to be observed in the field of view of the direct-view observation window 12 is formed at a central portion as a circular direct-view field of view image, and an image of the object to be observed in the field of view of the side-view observation window 13 is formed at an outer circumferential portion of the direct-view field of view image as a ring shaped side-view field of view image.

On the front end face of the distal end portion 6, a direct-view illumination window 16 which is disposed in a position adjacent to the cylindrical portion 10 and emits an illuminating light to the range of the direct-view field of view of the direct-view observation window 12, and a distal end opening portion 17 which communicates with a treatment instrument channel not illustrated which is formed by a tube or the like placed in the insertion section 4, and allows (a distal end portion of) a treatment instrument which is inserted through the treatment instrument channel to project, are provided.

Further, the distal end portion 6 of the insertion section 4 has a support portion 18 which is provided to be projected from the front end face of the distal end portion 6, and the support portion 18 is located adjacently to a lower portion side of the cylindrical portion 10.

The support portion 18 is configured to be able to support (or hold) respective projected members which are disposed to be projected from the front end face of the distal end portion 6. More specifically, the support portion 18 is configured to be able to support (or hold) a direct-view observation window nozzle portion 19 which emits a gas or a liquid for cleaning the direct-view observation window 12, a direct-view illumination window 21 which emits a light for illuminating the direct-view direction, and a side-view observation window nozzle portion 22 which emits a gas or a liquid for cleaning the side-view observation window 13, as the aforementioned respective projected members.

Meanwhile, the support portion 18 is formed by having a shielding portion 18a which is an optical shielding member for preventing a side-view field of view image including any of the respective projected members from being acquired due to appearance of the aforementioned respective projected members which are the matters different from the original object to be observed, in the side-view field of view. More specifically, as a result that the support portion 18 is provided with the shielding portion 18a, a side-view field of view image can be obtained, which does not include any of the direct-view observation window nozzle portion 19, the direct-view illumination window 21, and the side-view observation window nozzle portion 22.

Figure 3:
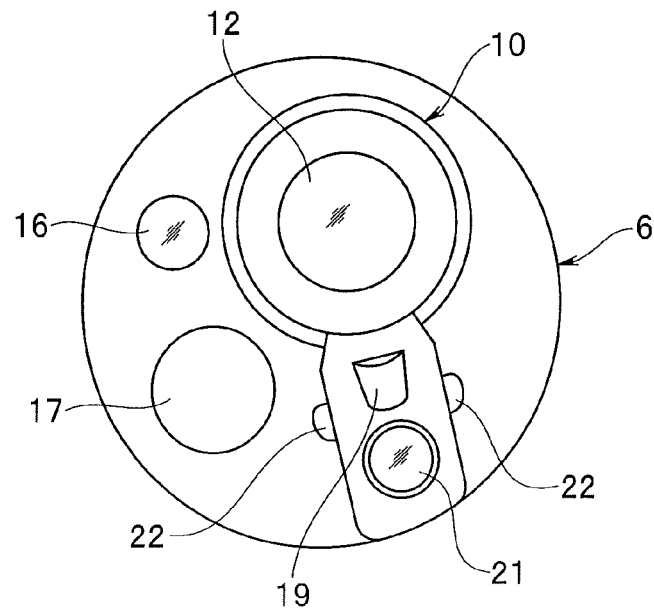
FIG. 3 is a front view showing the configuration of the distal end portion of the insertion section of the endoscope.

The side-view observation window nozzle portions 22 are provided at two locations of the support portion 18 as shown in FIGS. 2 and 3, and are disposed so that distal ends of the nozzle portions 22 are projected on a side face of the support portion 18.

As shown in FIG. 1, the operation section 3 is provided with a gas-supply/liquid supply operation button 24a capable of instructing an operation of emitting a gas or a liquid for cleaning the direct-view observation window 12 from the direct-view observation window nozzle portion 19, and a gas-supply/liquid-supply operation button 24b capable of instructing an operation of emitting a gas or a liquid for cleaning the side-view observation window 13 from the side-view observation window nozzle portion 22, and by depression of the gas-supply/liquid-supply operation buttons 24a and 24b, gas-supply and liquid supply can be switched. Further, in the present embodiment, a plurality of gas-supply/liquid-supply operation buttons are provided to correspond to the respective nozzle portions, but a gas or a liquid may be emitted from both the direct-view observation window nozzle portion 19 and the side-view observation window nozzle portion 22 by operation of one gas-supply/liquid-supply operation button, for example.

A plurality of scope switches 25 are provided at a top portion of the operation section 3, and each have a configuration capable of being assigned with a function of each switch so that signals corresponding to on or off of various functions usable in the endoscope 2 are outputted. More specifically, the scope switches 25 can be assigned with the functions of outputting the signals corresponding to start and stop of forward water supply, execution and release of freeze, notification of a use state of the treatment instrument and the like, for example, as the functions of the respective switches.

In the present embodiment, the function of at least any one of the gas-supply/liquid-supply operation buttons 24a and 24b may be assigned to any one of the scope switches 25.

A suction operation button 26 capable of performing an instruction for sucking and recovering mucus or the like in a body cavity from the distal end opening portion 17 for a suction unit or the like not illustrated is placed at the operation section 3.

Mucus or the like in a body cavity which is sucked in response to the operation of the suction unit or the like not illustrated is recovered into a suction bottle or the like of the suction unit not illustrated after passing through the distal end opening portion 17, the treatment instrument channel not illustrated in the insertion section 4 and a treatment instrument insertion port 27 provided in the vicinity of a front end of the operation section 3.

The treatment instrument insertion port 27 is formed as an opening which communicates with the treatment instrument channel not illustrated in the insertion section 4, and in which the treatment instrument not illustrated can be inserted. More specifically, a surgeon inserts the treatment instrument from the treatment instrument insertion port 27, and allows the distal end side of the treatment instrument to project from the distal end opening portion 17, whereby the surgeon can perform treatment using the treatment instrument.

Meanwhile, as shown in FIG. 1, a connector 29 which is connectable to a light source apparatus 31 is provided at the other end portion of the universal cord 5.

A pipe sleeve (not illustrated) to be a connection end portion of a fluid conduit, and a light guide pipe sleeve (not illustrated) to be a supply end portion of an illuminating light are provided at a distal end portion of the connector 29. Further, an electric contact section (not illustrated) to which one end portion of a connection cable 33 is connectable is provided on the side face of the connector 29. Furthermore, a connector for electrically connecting the endoscope 2 and a video processor 32 is provided at the other end portion of the connection cable 33.

The universal cord 5 contains a plurality of signal lines for transmitting various electrical signals, and a light guide for transmitting the illuminating light supplied from the light source apparatus 31 in a state tied in a bundle.

The aforesaid light guide contained in the insertion section 4 and the universal cord 5 has a configuration in which an end portion at a light exit side is branched into at least two directions in the vicinity of the insertion section 4, and a light exit end face at one side is disposed at the direct-view illumination windows 16 and 21, while a light exit end face at the other side is disposed at the side-view illumination portion 14. Further, the aforesaid light guide has a configuration in which the end portion at the light incident side is disposed at the light guide pipe sleeve of the connector 29.

Figure 4:
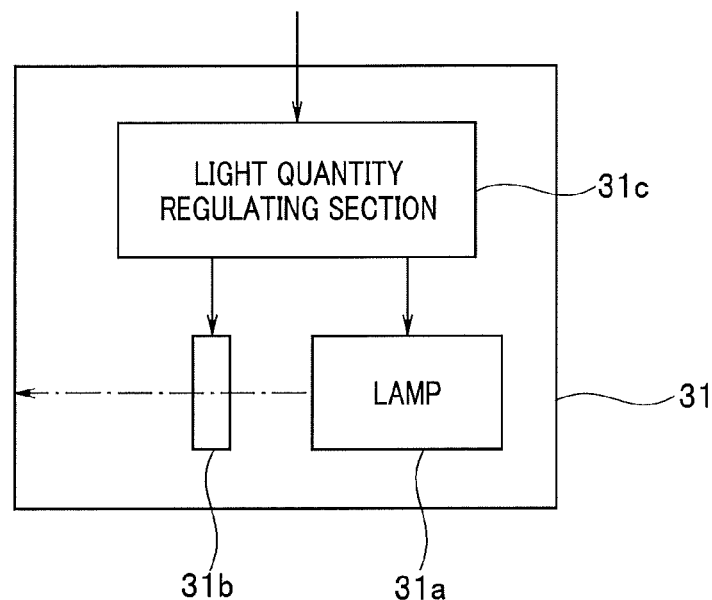
FIG. 4 is a block diagram showing a configuration of a light source apparatus.

As shown in FIG. 4, the light source apparatus 31 is configured by having a lamp 31*a* which emits an illuminating light for illuminating an object to be observed, a diaphragm 31*b* disposed on an optical path of the lamp 31*a*, and a light quantity regulating section 31*c* which changes at least one of a magnitude of a drive current for the lamp 31*a*, and a diaphragm value of the diaphragm 31*b* based on control of the video processor 32.

Figure 5:
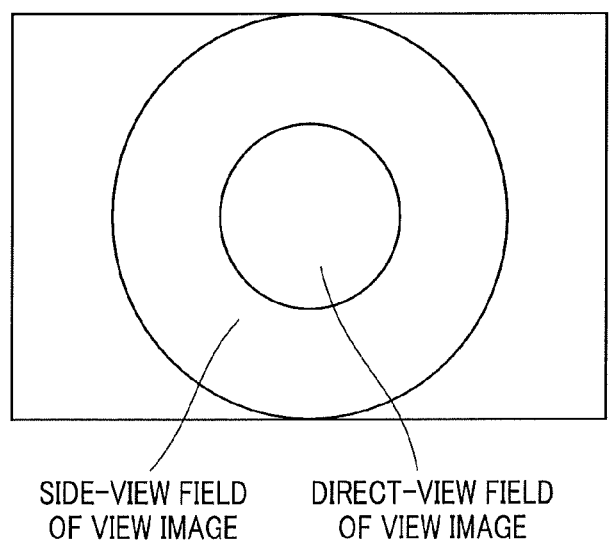
FIG. 5 is a view showing one example of an observed image displayed on a monitor.

The video processor 32 outputs a drive signal for driving the image pickup device provided at the distal end portion 6 of the endoscope 2. The video processor 32 generates a video signal by applying signal processing to an image pickup signal outputted from the aforesaid image pickup device to output the video signal to the monitor 35. Thereby, an observed image including a direct-view field of view image forming a circular shape, and a side-view field of view image forming a ring shape in the outer circumference of the image in the direct-view direction is displayed on the monitor 35 in the mode as shown in FIG. 5, for example. In the observed images shown in the present embodiment and the following embodiments, the portions which are optically shielded by the shielding portion 18*a* of the support portion 18 are not taken into consideration.

Meanwhile, based on the signal outputted from the scope switch 25, the video processor 32 can detect that one function corresponding to the signal is turned on or off (in an operation detection section 32*b* which will be described later).

Further, the video processor 32 detects the brightness of the direct-view field of view image and the brightness of the side-view field of view image in the observed image displayed on the monitor 35 individually whenever necessary. The video processor 32 controls the light source apparatus 31 to perform light adjustment until any one of the brightness of the direct-view field of view image and the brightness of the side-view field of view image reaches a predetermined brightness target value based on the factor which will be described in detail later.

The aforementioned predetermined brightness target value is assumed to be, for example, a value which is set in advance so that the image displayed on the monitor 35 has the optimal brightness, in accordance with the kind of observation (white light observation, special light observation or the like) which can be carried out by using the endoscope system 1.

The peripheral apparatuses such as the light source apparatus 31, the video processor 32 and the monitor 35 are disposed on a rack 36 with a keyboard 34 for performing input of patient information and the like.

Next, an operation of the present embodiment will be described.

Figure 6:
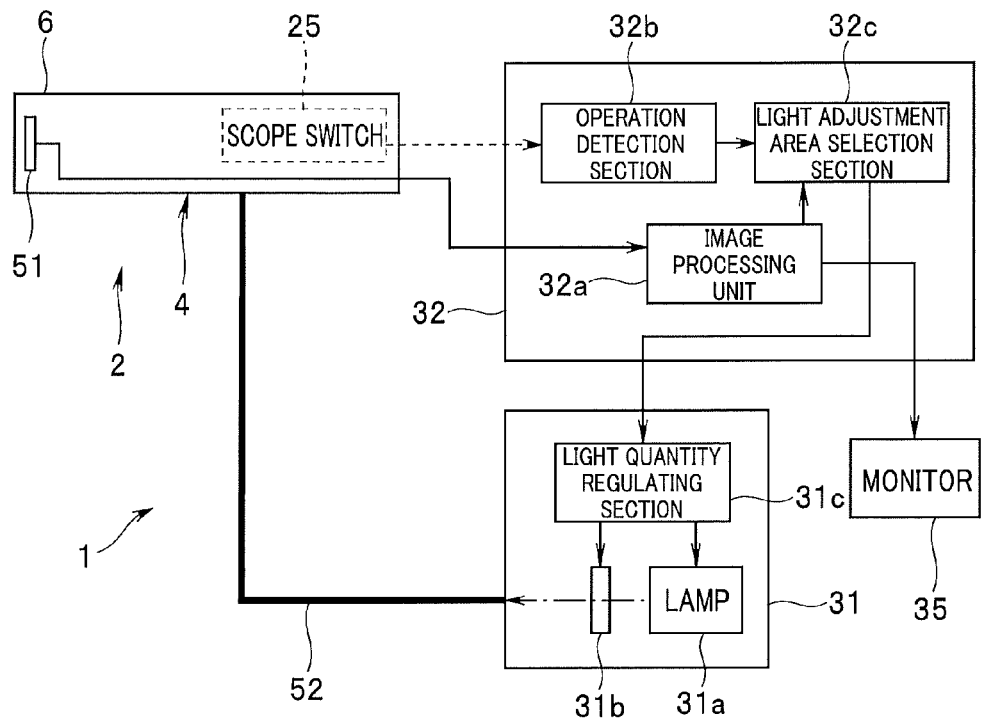
FIG. 6 is a diagram showing a configuration of an essential part in a first embodiment.

First, in the endoscope system 1 the main part of which is shown in FIG. 6, each part of an image pickup device 51 provided at the distal end portion 6 of the endoscope 2, the light source apparatus 31, the video processor 32 and the monitor 35 is actuated, and thereby, an image pickup signal is outputted from the image pickup device 51.

An image processing unit 32*a* (see FIG. 6) of the video processor 32 generates a video signal by applying signal processing to the image pickup signal outputted from the image pickup device 51, and outputs the video signal to a light adjustment area selection section 32*c* (see FIG. 6) and the monitor 35. Thereby, an observed image as shown in FIG. 5, for example, is displayed on the monitor 35.

Meanwhile, in order to perform treatment using a desired treatment instrument, a surgeon inserts the desired treatment instrument from the treatment instrument insertion port 27, and causes the distal end side of the desired treatment instrument to project from the distal end opening portion 17. With this, the surgeon operates the scope switch 25 at any time in the period until the surgeon causes the distal end side of the aforesaid desired treatment instrument to project from the distal end opening portion 17 and performs actual treatment after the surgeon inserts the aforesaid desired treatment instrument from the treatment instrument insertion port 27, and thereby, outputs a treatment instrument use informing signal for informing the video processor 32 of the intention to perform the treatment using the aforesaid desired treatment instrument.

The aforesaid treatment instrument use informing signal is not limited to the one that is outputted in response to the operation of the scope switch 25, and may be the one which is outputted as an output signal from an optical sensor provided in at least any one of the vicinity of the distal end opening portion 17 and the vicinity of the treatment instrument insertion port 27, for example.

The operation detection section 32*b* (see FIG. 6) of the video processor 32 detects that the treatment instrument is used in the endoscope 2 based on the treatment instrument use informing signal outputted from the scope switch 25, and outputs the detection result to the light adjustment area selection section 32c.

Meanwhile, the light adjustment area selection section 32c of the video processor 32 detects the brightness of the direct-view field of view image and the brightness of the side-view field of view image in the observed image displayed on the monitor 35 individually whenever necessary based on the video signal outputted from the image processing unit 32a.

When the detection result that the treatment instrument is used in the endoscope 2 is outputted from the operation detection section 32b, the light adjustment area selection section 32c performs control with respect to the light source apparatus 31 so that the brightness of the direct-view field of view image displayed on the monitor 35 reaches a predetermined brightness target value. In other words, when the detection result that the treatment instrument is used in the endoscope 2 is outputted from the operation detection section 32b, the light adjustment area selection section 32c of the video processor 32 selects the display area of the direct-view field of view image in the monitor 35 as the light adjustment target area, and sets the display area of the side-view field of view image in the monitor 35 as a non-light adjustment target area (refer to FIG. 11).

The light quantity regulating section 31c of the light source apparatus 31 changes at least one of the magnitude of the drive current of the lamp 31a and the diaphragm value of the diaphragm 31b so that the brightness of the light adjustment target area selected by the light adjustment area selection section 32c reaches the predetermined brightness target value. Thereby, the illuminating light with the light quantity which makes the brightness of the direct-view field of view image in the observed image the predetermined brightness target value is supplied to a light guide 52 from the light source apparatus 31.

Figure 11:
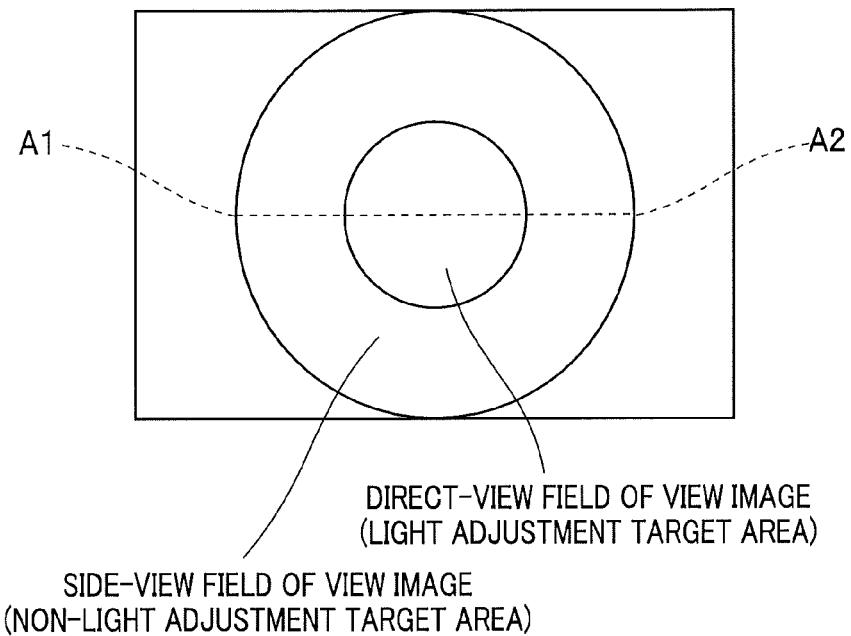
FIG. 11 is a view showing a case in which a direct-view field of view image is selected as a light adjustment target area in the observed image of FIG. 5.
Figure 12:
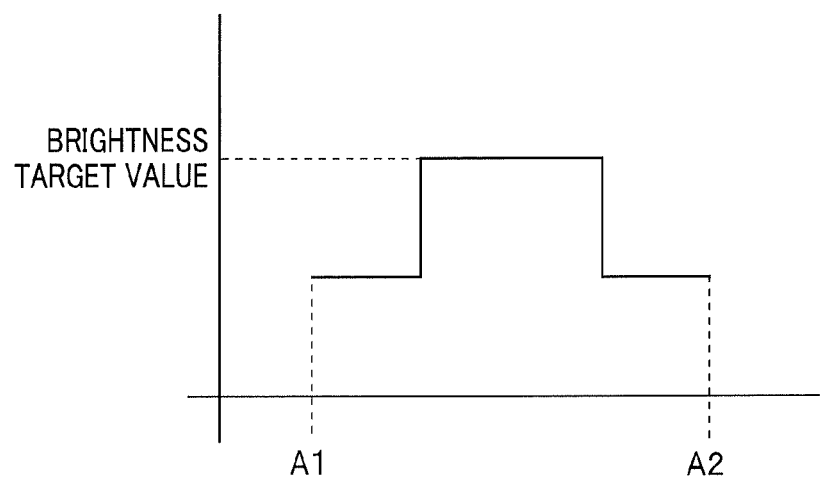
FIG. 12 is a diagram schematically showing a luminance (brightness) between A1 and A2 in the observed image of FIG. 11.

The control described above is performed for the light source apparatus 31, and thereby, the luminance (brightness) between A1 and A2 in the observed image shown in FIG. 11 becomes the luminance as shown in FIG. 12, for example. More specifically, as a result that the control as described above is performed for the light source apparatus 31, the luminance (brightness) of the display area of the direct-view field of view image in the monitor 35 becomes the luminance (brightness) corresponding to the predetermined brightness target value, and the luminance (brightness) of the display area of the side-view field of view image in the monitor 35 becomes the luminance (brightness) outside the predetermined brightness target value.

Here, when the endoscopy using a treatment instrument is performed, the method which projects the treatment instrument toward an affected part in the direct-view direction is generally adopted. According to the observed image including the luminance (brightness) as shown in FIG. 12, a series of operations of moving the treatment instrument close to the affected part by projecting the treatment instrument in the direct-view direction while watching the direct-view field of view image which has a suitable brightness can be smoothly performed.

The present embodiment is not limited to the one in which the display area of the direct-view field of image is selected as the light adjustment target area when treatment using a treatment instrument is performed, and may be the one in which the display area of the direct-view field of view image is selected as the light adjustment target area when the signal for instructing the start of forward supply of water is outputted from the scope switch 25, for example.

As described above, according to the present embodiment, the brightness of the image in one of the field of view directions in the observed image which can be simultaneously observed in the direct-view direction and the side-view direction can be properly regulated in accordance with at least one of the use state of the treatment instrument, and the operation state of the scope switch.

Second Embodiment

Next, a second embodiment of the present invention will be described.

In the subsequent description, the detailed description of the components having the same configurations as in the first embodiment will be omitted. An endoscope system of the present embodiment follows the external configuration as shown in FIGS. 1 to 3, the configuration of the light source apparatus shown in FIG. 4 and the display mode shown in FIG. 5 in the first embodiment, but includes some components differing from the components of the essential part shown in FIG. 6. Therefore, in the present embodiment, the part with the components differing from those of the essential part shown in FIG. 6 will be mainly described.

Figure 7:
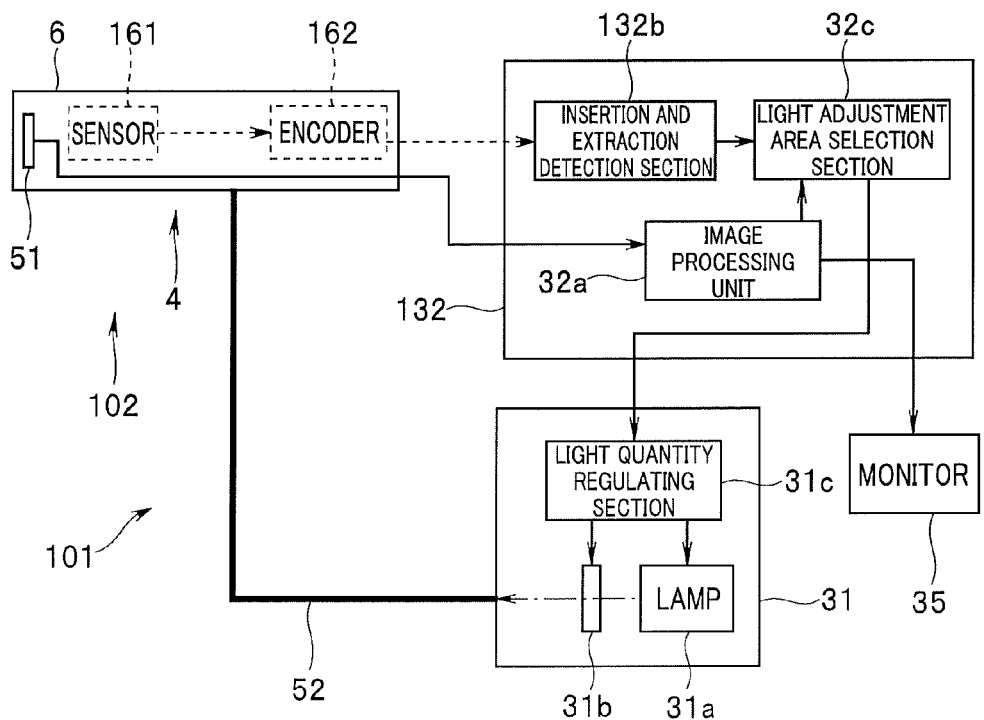
FIG. 7 is a diagram showing a configuration of an essential part in a second embodiment.

First, in an endoscope system 101 the essential part of which is shown in FIG. 7, each part of the image pickup device 51 provided at the distal end portion 6 of an endoscope 102, the light source apparatus 31, a video processor 132 and the monitor 35 is actuated, and thereby, an image pickup signal is outputted from the image pickup device 51.

The image processing unit 32a of the video processor 132 generates a video signal by applying signal processing to the image pickup signal outputted from the image pickup device 51, and outputs the video signal to the light adjustment area selection section 32c and the monitor 35. Thereby, the observed image as shown in FIG. 5, for example, is displayed on the monitor 35.

Meanwhile, a surgeon properly inserts or extracts the insertion section 4 of the endoscope 102 in a body cavity, and thereby, brings the distal end portion 6 close to a desired site in the body cavity.

A sensor 161 (refer to FIG. 7) which can detect information relating to a moving direction of the insertion section 4 as a physical quantity and output a signal is provided at the distal end portion 6 or in the vicinity thereof of the endoscope 102. More specifically, the sensor 161 is configured by an acceleration sensor capable of detecting and outputting a temporal displacement of the position of the insertion section 4 as an acceleration, an optical sensor capable of detecting and outputting a displacement amount (moving amount) per unit time of the position of the insertion section 4, or the like.

Further, an encoder 162 (refer to FIG. 7) capable of converting the information detected in the sensor 161 into an electrical signal and outputting the electrical signal to the video processor 132 is provided at the post-stage of the sensor 161 of the insertion section 4 of the endoscope 102.

An insertion and extraction detection section 132b (refer to FIG. 7) of the video processor 132 detects whether the moving direction of the insertion section 4 is forward (insertion direction) or rearward (extraction direction), based on the electrical signal outputted from the encoder 162, and outputs the detection result to the light adjustment area selection section 32c.

Meanwhile, the light adjustment area selection section 32c of the video processor 132 detects the brightness of the direct-view field of view image and the brightness of the side-view field of view image in the observed image displayed on the monitor 35 individually when necessary based on the video signal outputted from the image processing unit 32a.

When the detection result that the insertion section 4 is moving forward (insertion direction) is outputted from the insertion and extraction detection section 132b, the light adjustment area selection section 32c performs control with respect to the light source apparatus 31 until the brightness of the direct-view field of view image displayed on the monitor 35 reaches a predetermined brightness target value. In other words, when the detection result that the insertion section 4 is moving forward (insertion direction) is outputted from the insertion and extraction detection section 132b, the light adjustment area selection section 32c of the video processor 132 selects the display area of the direct-view field of view image in the monitor 35 as a light adjustment target area, and sets the display area of the side-view field of view image in the monitor 35 as a non-light adjustment target area (refer to FIG. 11).

The light quantity regulating section 31c of the light source apparatus 31 changes at least one of the magnitude of the drive current of the lamp 31a and the diaphragm value of the diaphragm 31b so that the brightness of the light adjustment target area selected by the light adjustment area selection section 32a reaches the predetermined brightness target value. Thereby, the illuminating light with the light quantity which makes the brightness of the direct-view field of view image in the observed image reach the predetermined brightness target value is supplied to the light guide 52 from the light source apparatus 31.

The control as described above is performed for the light source apparatus 31, and thereby, the luminance (brightness) between A1 and A2 in the observed image shown in FIG. 11 becomes the luminance as shown in FIG. 12, for example. That is to say, as a result that the control as described above is performed for the light source apparatus 31, the luminance (brightness) of the display area of the direct-view field of view image in the monitor 35 becomes the luminance (brightness) corresponding to the predetermined brightness target value, and the luminance (brightness) of the display area of the side-view field of view image in the monitor 35 becomes the luminance (brightness) outside the predetermined brightness target value.

Here, in the inserting operation of the insertion section, the situation which mainly requires attention to the direct-view direction can frequently occur. Thus, according to the observed image including the luminance (brightness) as shown in FIG. 12, the inserting operation of the insertion section 4 can be smoothly performed while the direct-view field of view image with a suitable brightness is being watched.

Further, when the detection result that the insertion section 4 is moving rearward (extraction direction) is outputted from the insertion and extraction detection section 132b, the light adjustment area selection section 32c performs control with respect to the light source apparatus 31 until the brightness of the side-view field of view image displayed on the monitor 35 reaches a predetermined brightness target value. In other words, when the detection result that the insertion section 4 is moving rearward (extraction direction) is outputted from the insertion and extraction detection section 132b, the light adjustment area selection section 32c of the video processor 132 selects the display area of the side-view field of view image in the monitor 35 as the light adjustment target area, and sets the display area of the direct-view field of view image in the monitor 35 as the non-light adjustment target area (refer to FIG. 13).

While the control by the light adjustment area selection section 32c is performed, the light quantity regulating section 31c of the light source apparatus 31 continues to change at least one of the magnitude of the drive current of the lamp 31a and the diaphragm value of the diaphragm 31b. At the time point when the control by the light adjustment area selection section 32c stops, the light quantity regulating section 31c fixes the magnitude of the drive current of the lamp 31a and the diaphragm value of the diaphragm 31b. Thereby, the illuminating light with the light quantity which makes the brightness of the side-view field of view image in the observed image reach the predetermined brightness target value is supplied to the light guide 52 from the light source apparatus 31.

Figure 13:
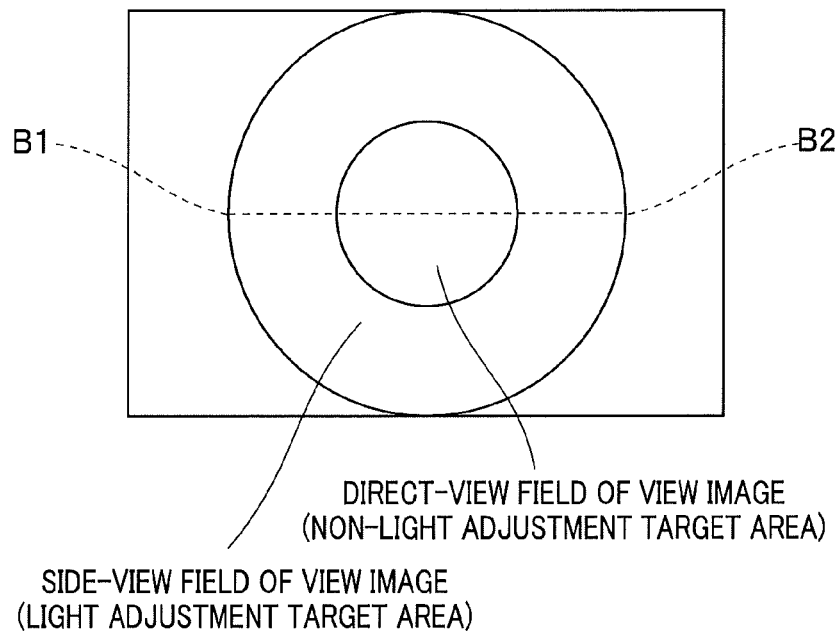
FIG. 13 is a view showing a case in which a side-view field of view image is selected as a light adjustment target area in the observed image of FIG. 5.
Figure 14:
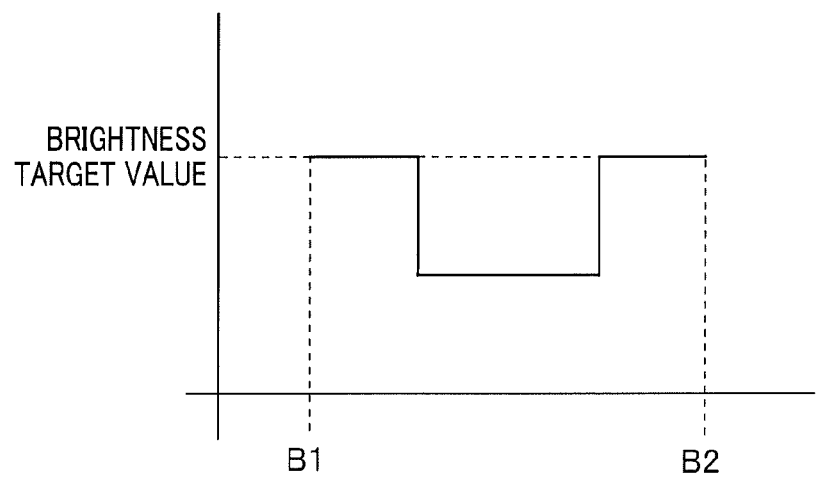
FIG. 14 is a diagram schematically showing a luminance (brightness) between B1 and B2 in the observed image of FIG. 13.

The control as described above is performed for the light source apparatus 31, and thereby, the luminance (brightness) between B1 and B2 in the observed image shown in FIG. 13 becomes the one as shown in FIG. 14, for example. That is to say, the control as described above is performed for the light source apparatus 31, whereby the luminance (brightness) of the display area of the side-view field of view image in the monitor 35 becomes the luminance (brightness) corresponding to the predetermined brightness target value, and the luminance (brightness) of the display area of the direct-view field of view image in the monitor 35 becomes the luminance (brightness) outside the predetermined brightness target value.

Here, in the extracting operation of the insertion section, the situation which mainly requires attention to the side-view direction can frequently take place. Thus, according to the observed image including the luminance (brightness) as shown in FIG. 14, the extracting operation of the insertion section 4 can be smoothly performed while the side-view field of view image with a suitable brightness is being watched.

Figure 8:
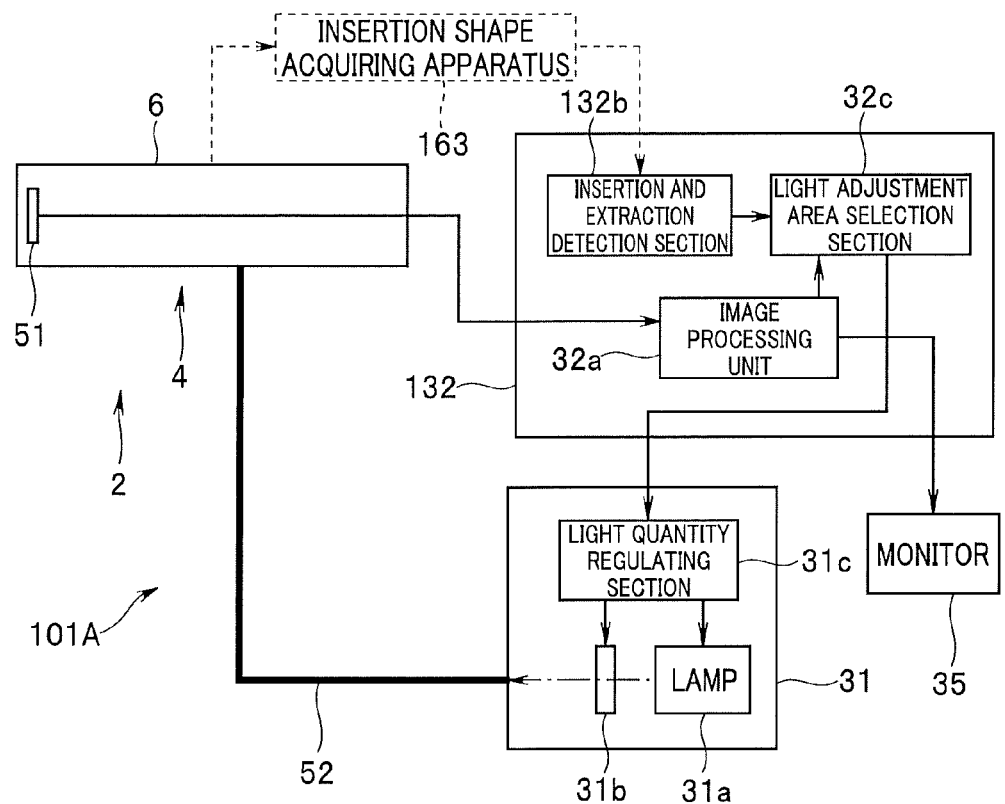
FIG. 8 is a diagram showing a configuration of an essential part in a modified example of the second embodiment.

According to the present embodiment, the endoscope system may be the one which is configured as an endoscope system 101A of FIG. 8 which acquires information relating to the moving direction of the insertion section 4 of the endoscope 2 by using, for example, an insertion shape acquiring apparatus 163, instead of the endoscope system 101 of FIG. 7 which is configured by including the sensor 161 and the encoder 162.

More specifically, the insertion shape acquiring apparatus 163 of the endoscope system 101A the essential part of which is shown in FIG. 8 is configured as, for example, an x-ray image pickup apparatus which is capable of acquiring an x-ray image of the insertion section 4 and outputting a signal to the insertion and extraction detection section 132b. In this case, the insertion and extraction detection section 132b detects whether the moving direction of the insertion section 4 is forward (insertion direction) or rearward (extraction direction) by comparing two x-ray images adjacent to each other in time series out of the x-ray images of the insertion section 4 which are sequentially outputted as signals from the insertion shape acquiring apparatus 163, and outputs the detection result to the light adjustment area selection section 32c, for example.

Alternatively, the insertion shape acquiring apparatus 163 is configured, for example, as an endoscope insertion shape detecting apparatus which is capable of detecting a magnetic field generated in response to drive of a plurality of magnetic field generating elements (not illustrated) disposed in the insertion section 4 in a magnetic field detection section (not illustrated), and generating an insertion shape image of the insertion section 4 corresponding to the magnetic field to output a signal to the insertion and extraction detection section 132b. In this case, the insertion and extraction detection section 132b detects whether the moving direction of the insertion section 4 is forward (insertion direction) or rearward (extraction direction) by comparing two insertion shape images adjacent to each other in time series out of the insertion shape images of the insertion section 4 which are sequentially outputted as signals from the insertion shape acquiring apparatus 163, for example, and outputs the detection result to the light adjustment area selection section 32c.

As described above, according to the present embodiment, the brightness of the image of one of the field of view directions in the observed image which can be simultaneously observed in the direct-view direction and the side-view direction can be properly regulated in accordance with the inserting operation and extracting operation of the insertion section of the endoscope.

Third Embodiment

Next, a third embodiment of the present invention will be described.

In the subsequent description, the detailed description of the components having the same configurations as in the first embodiment or the second embodiment will be omitted. An endoscope system of the present embodiment follows the external configuration as shown in FIGS. 1 to 3, the configuration of the light source apparatus shown in FIG. 4 and the display mode shown in FIG. 5 respectively, but includes some components differing from the components of the essential part shown in FIG. 6. Therefore, in the present embodiment, the part with the components differing from those of the essential part shown in FIG. 6 will be mainly described.

Figure 9:
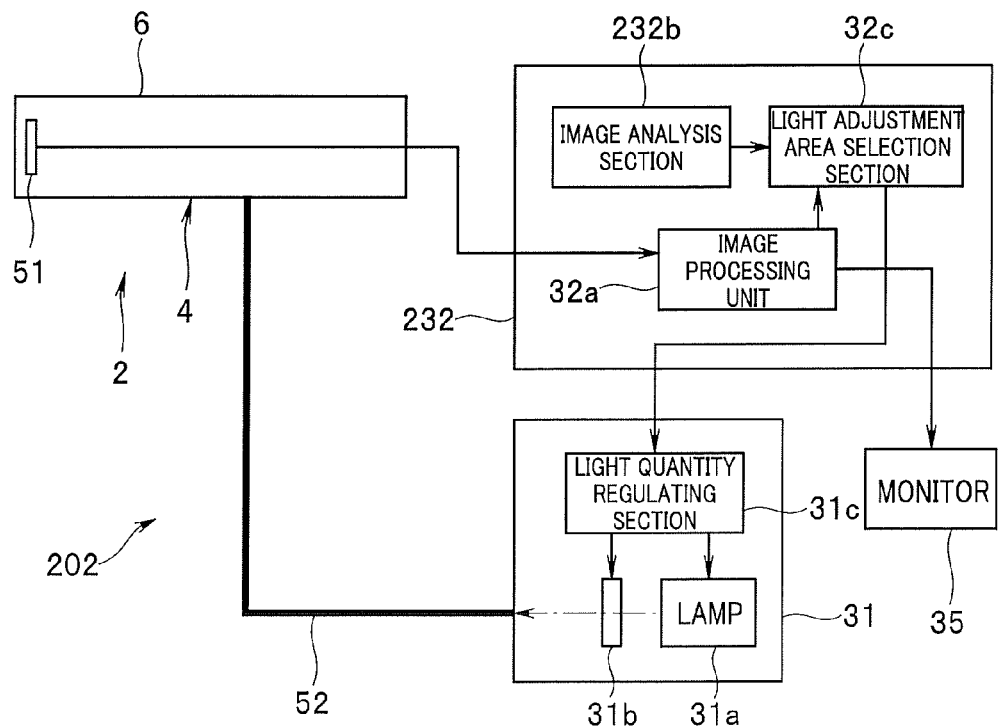
FIG. 9 is a diagram showing a configuration of an essential part in a third embodiment.

First, in an endoscope system 201 the essential part of which is shown in FIG. 9, each part of the image pickup device 51 provided at the distal end portion 6 of the endoscope 2, the light source apparatus 31, a video processor 232 and the monitor 35 is actuated, and thereby, an image pickup signal is outputted from the image pickup device 51.

The image processing unit 32a of the video processor 232 generates a video signal by applying signal processing to the image pickup signal outputted from the image pickup device 51, and outputs the video signal to an image analysis section 232b (refer to FIG. 9), the light adjustment area selection section 32c and the monitor 35. Thereby, the observed image as shown in FIG. 5, for example, is displayed on the monitor 35.

The image analysis section 232b of the video processor 232 is set in advance to designate an object including a predetermined color, or an object including a predetermined luminance as a landmark in the observed image corresponding to the video signal outputted from the image processing unit 32a.

Further, the image analysis section 232b detects whether the aforementioned landmark is moving to an outer edge side, or a central side of the observed image by comparing two frames of the observed image adjacent to each other in time series, for example, and outputs the detection result to the light adjustment area selection section 32c. More specifically, the image analysis section 232b detects the moving direction of the aforementioned landmark by performing calculation using a spatial gradient or a temporal gradient (optical flow) of the luminance in the observed image, for example, and outputs the detection result to the light adjustment area selection section 32c.

Meanwhile, the light adjustment area selection section 32c of the video processor 232 detects the brightness of the direct-view field of view image and the brightness of the side-view field of view image in the observed image displayed on the monitor 35 individually whenever necessary, based on the video signal outputted from the image processing unit 32a.

When the detection result that the aforementioned landmark is moving to the outer edge side of the observed image is outputted from the image analysis section 232b, the light adjustment area selection section 32c performs control with respect to the light source apparatus 31 until the brightness of the direct-view field of view image displayed on the monitor 35 reaches a predetermined brightness target value. In other words, when the detection result that the aforementioned landmark is moving to the outer edge side of the observed image is outputted from the image analysis section 232b, (since the insertion section 4 is estimated to be inserted,) the light adjustment area selection section 32c of the video processor 232 selects the display area of the direct-view field of view image in the monitor 35 as a light adjustment target area, and sets the display area of the side-view field of view image in the monitor 35 as a non-light adjustment target area (refer to FIG. 11).

The light quantity regulating section 31c of the light source apparatus 31 changes at least one of the magnitude of the drive current of the lamp 31a and the diaphragm value of the diaphragm 31b so that the brightness of the light adjustment target area selected by the light adjustment area selection section 32c reaches the predetermined brightness target value. Thereby, the illuminating light with the light quantity which makes the brightness of the direct-view field of view image in the observed image reach the predetermined brightness target value is supplied to the light guide 52 from the light source apparatus 31.

The control as described above is performed for the light source apparatus 31, and thereby, the luminance (brightness) between A1 and A2 in the observed image shown in FIG. 11 becomes the luminance as shown in FIG. 12, for example. That is to say, as a result that the control as described above is performed for the light source apparatus 31, the luminance (brightness) of the display area of the direct-view field of view image in the monitor 35 becomes the luminance (brightness) corresponding to the predetermined brightness target value, and the luminance (brightness) of the display area of the side-view field of view image in the monitor 35 becomes the luminance (brightness) outside the predetermined brightness target value.

Here, in the inserting operation of the insertion section, the situation which mainly requires attention to the direct-view direction can frequently occur. Thus, according to the observed image including the luminance (brightness) as shown in FIG. 12, the inserting operation of the insertion section 4 can be smoothly performed while the direct-view field of view image with a suitable brightness is being watched.

Further, when the detection result that the aforementioned landmark is moving to the central side of the observed image is outputted from the image analysis section 232b, the light adjustment area selection section 32c performs control with respect to the light source apparatus 31 until the brightness of the side-view field of view image displayed on the monitor 35 reaches a predetermined brightness target value. In other words, when the detection result that the aforementioned landmark is moving to the central side of the observed image is outputted from the image analysis section 232b, (since the insertion section 4 is estimated to be extracted,) the light adjustment area selection section 32c of the video processor 232 selects the display area of the side-view field of view image in the monitor 35 as the light adjustment target area, and sets the display area of the direct-view field of view image in the monitor 35 as the non-light adjustment target area (refer to FIG. 13).

The light quantity regulating section 31c of the light source apparatus 31 changes at least one of the magnitude of the drive current of the lamp 31a and the diaphragm value of the diaphragm 31b so that the brightness of the light adjustment target area selected by the light adjustment area selection section 32c reaches the predetermined brightness target value. Thereby, the illuminating light with the light quantity which makes the brightness of the side-view field of view image in the observed image reach the predetermined brightness target value is supplied to the light guide 52 from the light source apparatus 31.

The control as described above is performed for the light source apparatus 31, and thereby, the luminance (brightness) between B1 and B2 in the observed image shown in FIG. 13 becomes the luminance as shown in FIG. 14, for example. That is to say, the control as described above is performed for the light source apparatus 31, whereby the luminance (brightness) of the display area of the side-view field of view image in the monitor 35 reaches the luminance (brightness) corresponding to the predetermined brightness target value, and the luminance (brightness) of the display area of the direct-view field of view image in the monitor 35 becomes the luminance (brightness) outside the predetermined brightness target value.

Here, in the extracting operation of the insertion section, the situation which mainly requires attention to the side-view direction can frequently occur. According to the observed image including the luminance (brightness) as shown in FIG. 14, the extracting operation of the insertion section 4 can be smoothly performed while the side-view field of view image with a suitable brightness is being watched.

The image analysis section 232b may be the one that outputs the detection result that the aforementioned landmark is not moving, other than the detection result that the aforementioned landmark is moving to either the outer edge side or the central side of the observed image. In accordance with this, the light adjustment area selection section 32c may be the one that keeps the light adjustment target area to be the same display area as selected at the previous time, when the light adjustment area selection section 32c obtains the detection result that the aforementioned landmark is not moving from the image analysis section 232b (since the insertion section 4 is estimated to be not moving).

Further, the image analysis section 232b of the present embodiment is not limited to the one that detects whether the aforementioned landmark is moving to the outer edge side, or the central side of the observed image, and may be the one that detects the temporal change of the size of the aforementioned landmark in the observed image by comparing two frames of the observed image adjacent to each other in time series, for example. In accordance with this, the light adjustment area selection section 32c may be the one that selects the display area of the direct-view field of view image as the light adjustment target area when the light adjustment area selection section 32c obtains the detection result that the size of the aforementioned landmark gradually becomes larger from the image analysis section 232b, selects the display area of the side-view field of view image as the light adjustment target area when obtaining the detection result that the size of the aforementioned landmark gradually becomes smaller from the image analysis section 232b, and further, keeps the light adjustment target area to be the same display area as selected at the previous time when obtaining the detection result that the size of the aforementioned landmark does not change from the image analysis section 232b (since the insertion section 4 is estimated to be not moving).

Figure 15:
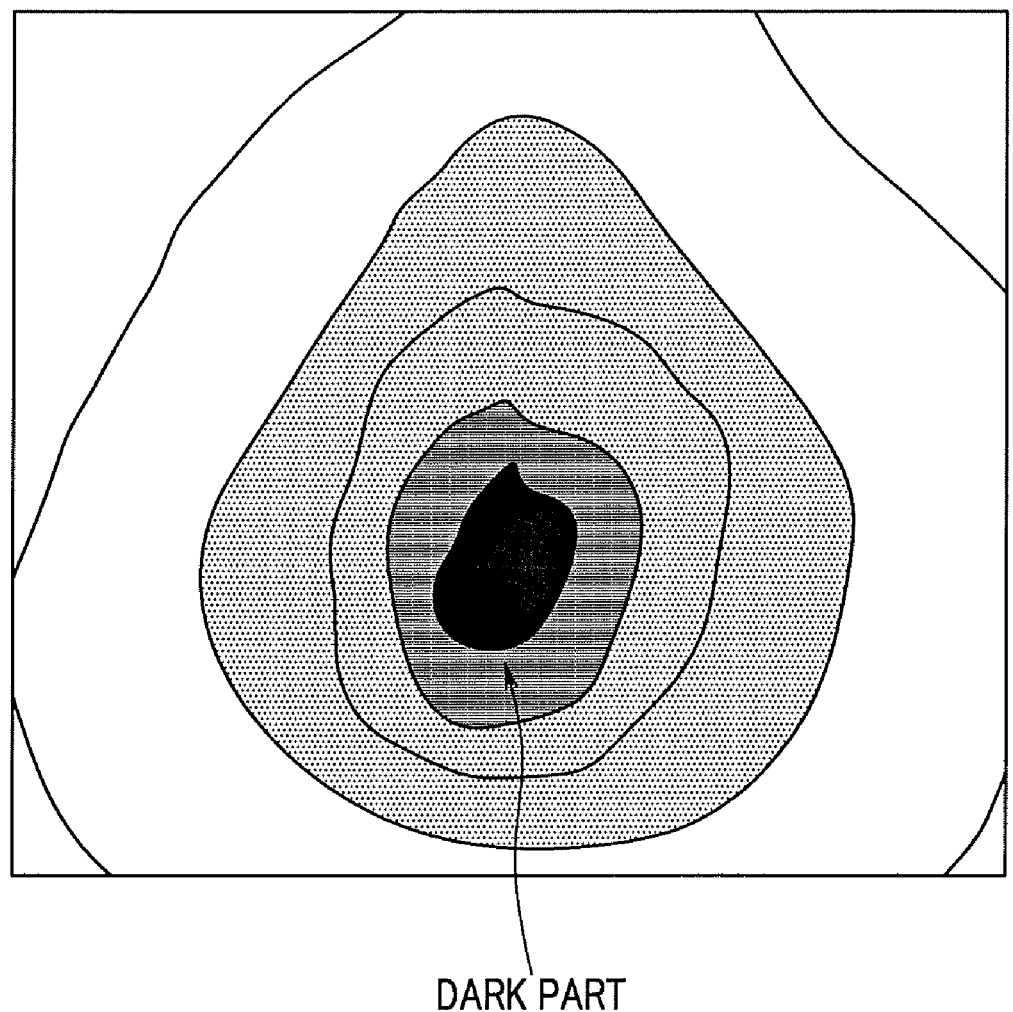
FIG. 15 is a view showing one example of an image including a dark part in a lumen.

Furthermore, as shown in FIG. 15, for example, when a luminal interior is observed by using an endoscope, the deep inner side in the traveling direction (deep part in the opening direction) of the insertion section inserted in the lumen is displayed on the image as a dark part since the illuminating light for observation hardly reaches the deep inner side. The image analysis section 232b of the present embodiment may be the one that uses this, sets a dark part on the image as a landmark, and thereby, detects whether the dark part (the traveling direction of the insertion section 4 inserted in the lumen) is located in the direct-view field of view image, or the side-view field of view image of the present observed image. In accordance with this, the light adjustment area selection section 32c may be the one that selects the display area of the direct-view field of view image as the light adjustment target area when obtaining the detection result that the dark part is present in the direct-view field of view image from the image analysis section 232b, and selects the display area of the side-view field of view image as the light adjustment target area when obtaining the detection result that the dark part is present in the side-view field of view image from the image analysis section 232b.

Meanwhile, the image analysis section 232b of the present embodiment is not limited to the one that detects the moving direction and the like of the aforementioned landmark, and may be the one that detects whether or not electronic zoom processing is applied to the present observed image, based on the video signal outputted from the image processing unit 32a, for example. In accordance with this, the light adjustment area selection section 32c may be the one that selects the display area of the direct-view field of view image as the light adjustment target area when obtaining the detection result that electronic zoom processing is applied to the observed image from the image analysis section 232b.

As described above, according to the present embodiment, the brightness of the image of one of the field of view directions in the observed image which can be simultaneously observed in the direct-view direction and the side-view direction can be properly regulated in accordance with the present observation situation of the endoscope.

Fourth Embodiment

Next, a fourth embodiment of the present invention will be described.

In the subsequent description, the detailed description of the components having the same configurations as in the first embodiment, the second embodiment, or the third embodiment will be omitted. Further, an endoscope system of the present embodiment follows the external configuration as shown in FIGS. 1 to 3, the configuration of the light source apparatus shown in FIG. 4 and the display mode shown in FIG. 5, but includes some components differing from the components of the essential part shown in FIG. 6. Therefore, in the present embodiment, the part with the components differing from those of the essential part shown in FIG. 6 will be mainly described.

Figure 10:
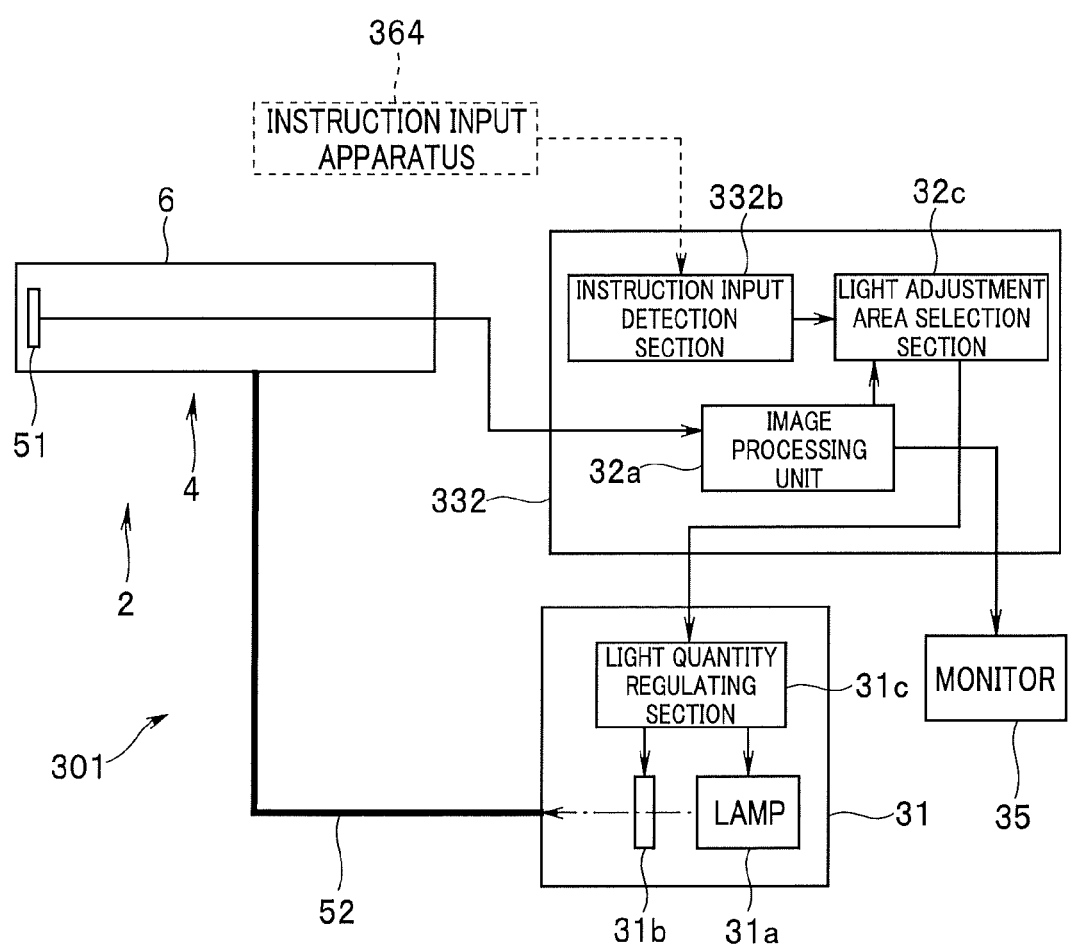
FIG. 10 is a diagram showing a configuration of an essential part in a fourth embodiment.

First, in an endoscope system 301 the essential part of which is shown in FIG. 10, each part of the image pickup device 51 provided at the distal end portion 6 of the endoscope 2, the light source apparatus 31, a video processor 332 and the monitor 35 is actuated, and thereby, an image pickup signal is outputted from the image pickup device 51.

The image processing unit 32a of the video processor 332 generates a video signal by applying signal processing to the image pickup signal outputted from the image pickup device 51, and outputs the video signal to the light adjustment area selection section 32c and the monitor 35. Thereby, the observed image as shown in FIG. 5, for example, is displayed on the monitor 35.

A surgeon performs an instruction for applying a suitable brightness to one of the direct-view field of view image or the side-view field of view image of the observed image displayed on the monitor 35, by the input operation to an instruction input apparatus 364. The instruction input apparatus 364 may be configured as a single apparatus, or may be incorporated in any of the apparatuses included by the endoscope system 301, as long as it is an apparatus capable of outputting signals corresponding to on, off or the like of various functions usable in the endoscope 2. More specifically, the instruction input apparatus 364 may be any of the scope switch 25, the keyboard 34, the operation panel of the video processor 332, and a foot switch.

An instruction input detection section 332b of the video processor 332 detects whether the instruction performed in the instruction input apparatus 364 is the instruction for applying a suitable brightness to the direct-view field of view image, or the instruction for applying a suitable brightness to the side-view field of view image, and outputs the detection result to the light adjustment area selection section 32c.

Meanwhile, the light adjustment area selection section 32c of the video processor 332 detects the brightness of the direct-view field of view image and the brightness of the side-view field of view image in the observed image displayed on the monitor 35 individually whenever necessary, based on the video signal outputted from the image processing unit 32a.

When the detection result that the instruction for applying a suitable brightness to the direct-view field of view image is performed is outputted from the instruction input detection section 332b, the light adjustment area selection section 32c performs control with respect to the light source apparatus 31 until the brightness of the direct-view field of view image displayed on the monitor 35 reaches a predetermined brightness target value. In other words, when the detection result that the instruction for applying the suitable brightness to the direct-view field of view image is performed is outputted from the instruction input detection section 332b, the light adjustment area selection section 32c of the video processor 332 selects the display area of the direct-view field of view image in the monitor 35 as a light adjustment target area, and sets the display area of the side-view field of view image in the monitor 35 as a non-light adjustment target area (refer to FIG. 11).

The light quantity regulating section 31c of the light source apparatus 31 changes at least one of the magnitude of the drive current of the lamp 31a and the diaphragm value of the diaphragm 31b so that the brightness of the light adjustment target area selected by the light adjustment area selection section 32c reaches the predetermined brightness target value. Thereby, the illuminating light with the light quantity which makes the brightness of the direct-view field of view image in the observed image reach the predetermined brightness target value is supplied to the light guide 52 from the light source apparatus 31.

The control as described above is performed for the light source apparatus 31, and thereby, the luminance (brightness) between A1 and A2 in the observed image shown in FIG. 11 becomes the one as shown in FIG. 12, for example. That is to say, as a result that the control as described above is performed for the light source apparatus 31, the luminance (brightness) of the display area of the direct-view field of view image in the monitor 35 becomes the luminance (brightness) corresponding to the predetermined brightness target value, and the luminance (brightness) of the display area of the side-view field of view image in the monitor 35 becomes the luminance (brightness) outside the predetermined brightness target value.

Further, when the detection result that the instruction for applying a suitable brightness to the side-view field of view image is performed is outputted from the instruction input detection section 332b, the light adjustment area selection section 32c performs control with respect to the light source apparatus 31 until the brightness of the side-view field of view image displayed on the monitor 35 reaches a predetermined brightness target value. In other words, when the detection result that the instruction for applying the suitable brightness to the side-view field of view image is performed is outputted from the instruction input detection section 332b, the light adjustment area selection section 32c of the video processor 332 selects the display area of the side-view field of view image in the monitor 35 as the light adjustment target area, and sets the display area of the direct-view field of view image in the monitor 35 as the non-light adjustment target area (refer to FIG. 13).

The light quantity regulating section 31c of the light source apparatus 31 changes at least one of the magnitude of the drive current of the lamp 31a and the diaphragm value of the diaphragm 31b so that the brightness of the light adjustment target area selected by the light adjustment area selection section 32c reaches the predetermined brightness target value. Thereby, the illuminating light with the light quantity which makes the brightness of the side-view field of view image in the observed image reach the predetermined brightness target value is supplied to the light guide 52 from the light source apparatus 31.

The control as described above is performed for the light source apparatus 31, and thereby, the luminance (brightness) between B1 and B2 in the observed image shown in FIG. 13 becomes the luminance as shown in FIG. 14, for example. That is to say, the control as described above is performed for the light source apparatus 31, whereby the luminance (brightness) of the display area of the side-view field of view image in the monitor 35 becomes the luminance (brightness) corresponding to the predetermined brightness target value, and the luminance (brightness) of the display area of the direct-view field of view image in the monitor 35 becomes the luminance (brightness) outside the predetermined brightness target value.

The instruction input apparatus 364 is not limited to the one configured by the aforementioned respective apparatuses, and may be the one that is configured by a microphone capable of taking in the voice of a surgeon as a sound signal, for example. In accordance with this, the instruction input detection section 332b may be the one that detects whether the instruction for applying a suitable brightness to the direct-view field of view image, or the instruction for applying the suitable brightness to the side-view field of view image is performed by performing sound analysis processing for the sound signal outputted from the instruction input apparatus 364.

Further, in the present embodiment, the instruction input apparatus 364 may be configured so as to be able to perform an instruction for averaging the brightness of the direct-view field of view image and the brightness of the side-view field of view image, in addition to the instruction for applying a suitable brightness to the direct-view field of view image and the instruction for applying the suitable brightness to the side-view field of view image. In such a case, the light adjustment area selection section 32c sets the entire display area including both the direct-view field of view image and the side-view field of view image as the light adjustment target area.

As described above, according to the present embodiment, in the observed image which can be simultaneously observed in the direct-view direction and the side-view direction, the brightness of the image in the desired field of view direction can be regulated to be a suitable brightness. Further, switch control of the light adjustment target area by the input operation for the instruction input apparatus 364 of the present embodiment may be used in combination with automatic switch control as in the first through third embodiments. In such a case, light adjustment of the desired display area of the surgeon can be properly performed by giving a higher priority to switch by the input operation for the instruction input apparatus 364 than automatic switch control, for example.

The present invention is not limited to the aforementioned respective embodiments, and various modifications and applications can be made within the range without departing from the gist of the invention as a matter of course.

What is claimed is:

1. An endoscope system, comprising:
    an endoscope which acquires a direct-view field of view image and a side-view field of view image of an object to be observed in a body cavity;
    a light source apparatus which supplies an illuminating light for illuminating the object to be observed;
    a sensor section which detects a change of a physical quantity indicative of a moving direction of an insertion direction or an extraction direction of an insertion section with respect to the object to be observed in the body cavity, the insertion section being provided at the endoscope, and the change of the physical quantity occurring due to an operation of the endoscope;
    an image processing unit which generates an observed image including the direct-view field of view image and the side-view field of view image in a same screen, and outputs the observed image as a video signal;
    a detection section which detects a brightness of the direct-view field of view image and a brightness of the side-view field of view image individually based on the video signal;
    an insertion/extraction detection section which detects whether the moving direction of the insertion section is the insertion direction or the extraction direction based on a detection result of the sensor section;
    a light adjustment area selection section which selects the direct-view field of view image as a light adjustment target when the moving direction of the insertion section is the insertion direction, and selects the side-view field of view image as the light adjustment target when the moving direction of the insertion section is the extraction direction based on a detection result of the insertion/extraction detection section; and
    a light quantity adjusting section which performs control so as to make a luminance of the field of view image selected as the light adjustment target relatively higher than a luminance of the other field of view image.

2. The endoscope system according to claim 1, further comprising:
    an insertion shape acquiring apparatus which acquires an insertion shape of the insertion section,
    wherein the sensor section detects that the insertion section is inserted or extracted based on a signal including the insertion shape of the insertion section obtained in the insertion shape acquiring apparatus.

3. The endoscope system according to claim 1,
    wherein the sensor section detects information relating to a predetermined landmark included in the observed image based on the video signal, and
    the light adjustment area selection section selects the one field of view image as a light adjustment target based on a detection result of the information relating to the predetermined landmark, and
    the light quantity adjusting section performs control with respect to the light source apparatus so that the one field of view image reaches a predetermined brightness target value.

4. The endoscope system according to claim 3,
    wherein the sensor section detects a moving direction of the predetermined landmark in the observed image.

5. The endoscope system according to claim 3,
    wherein the sensor section detects a change with time of a size of the predetermined landmark in the observed image.

6. The endoscope system according to claim 3,
    wherein the sensor section detects a position where the predetermined landmark is present in the observed image.

* * * * *